(12) United States Patent
Kim

(10) Patent No.: US 8,361,717 B2
(45) Date of Patent: Jan. 29, 2013

(54) MAGNETIC PARTICLES FOR NUCLEIC ACID SEQUENCING AND METHOD OF SEQUENCING NUCLEIC ACID USING THE SAME

(75) Inventor: Su-hyeon Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 356 days.

(21) Appl. No.: 12/580,325

(22) Filed: Oct. 16, 2009

(65) Prior Publication Data
US 2010/0291558 A1 Nov. 18, 2010

(30) Foreign Application Priority Data

May 12, 2009 (KR) .................. 10-2009-0041365

(51) Int. Cl.
*C12Q 1/68* (2006.01)
*C12M 1/00* (2006.01)
*C07H 21/02* (2006.01)
*C07H 21/04* (2006.01)

(52) U.S. Cl. .............. 435/6.1; 435/283.1; 536/23.1; 536/24.3

(58) Field of Classification Search ............ 435/6, 91.2, 435/283.1, 6.1; 536/23.1, 24.3
See application file for complete search history.

(56) References Cited

U.S. PATENT DOCUMENTS

| | | | |
|---|---|---|---|
| 4,876,187 A * | 10/1989 | Duck et al. ............ | 435/5 |
| 5,256,775 A * | 10/1993 | Froehler ............ | 536/25.6 |
| 6,977,295 B2 * | 12/2005 | Belotserkovskii et al. .. | 536/23.1 |
| 7,279,285 B2 * | 10/2007 | Holmberg ............ | 435/7.1 |
| 2001/0029293 A1 * | 10/2001 | Gallatin et al. ............ | 530/387.3 |
| 2002/0164659 A1 * | 11/2002 | Rao et al. ............ | 435/7.5 |
| 2004/0058458 A1 * | 3/2004 | Anker et al. ............ | 436/526 |
| 2006/0223083 A1 * | 10/2006 | Dale ............ | 435/6 |
| 2007/0166835 A1 * | 7/2007 | Bobrow et al. ............ | 436/174 |
| 2008/0003571 A1 * | 1/2008 | McKernan et al. ............ | 435/6 |
| 2008/0188374 A1 * | 8/2008 | Chen et al. ............ | 506/2 |
| 2008/0319678 A1 * | 12/2008 | Templeton et al. ............ | 702/19 |
| 2009/0186356 A1 * | 7/2009 | Wendel et al. ............ | 435/6 |
| 2010/0129810 A1 * | 5/2010 | Greiner et al. ............ | 435/6 |
| 2010/0331199 A1 * | 12/2010 | Stoll et al. ............ | 506/9 |

FOREIGN PATENT DOCUMENTS

DE 3816934 A1 11/1989
WO 9001562 A1 2/1990

OTHER PUBLICATIONS

Schatz et al., HIV-1 RT-associated ribonuclease Hdisplays both endonuclease and 3' to 5' exonuclease activity. EMBO Journal 9 (4) : 1171 (1990).*
European Extended Search Report and Opinion; Application No. 10153186.1 dated Jul. 8, 2010.
Jarvie, T., Next generation sequencing technologies, Drug Discovery Today: Technologies, vol. 2, Issue 3, 2005, 247-252.
Syvänen, A.C. et al., Genetic analysis of the polymorphism of the human apolipoprotein E using automated solid-phase sequencing, Genet Anal Tech Appl. Jun. 1991; 8(4):117-23.
Teles, F.R.R. et al., Trends in DNA biosensors, Talanta, vol. 77, Issue 2, Dec. 15, 2008, 606-623.

* cited by examiner

*Primary Examiner* — Ethan C Whisenant
(74) *Attorney, Agent, or Firm* — Leydig, Voit & Mayer, Ltd.

(57) ABSTRACT

Provided are magnetic particles for nucleic acid sequencing and a method of sequencing nucleic acid using the same. The nucleotide sequence of a target nucleic acid may be efficiently determined using the magnetic particles and the method of sequencing nucleic acid using the same.

16 Claims, 4 Drawing Sheets

MAGNETIC PARTICLES FOR NUCLEIC ACID SEQUENCING AND METHOD OF SEQUENCING NUCLEIC ACID USING THE SAME

CROSS-REFERENCE TO RELATED APPLICATIONS

This application claims priority to Korean Patent Application No. 10-2009-0041365, filed on May 12, 2009, and all the benefits accruing therefrom under 35 U.S.C. §119, the contents of which is incorporated herein in its entirety by reference.

BACKGROUND

1. Field

One or more embodiments of the invention relate to a magnetic particle for sequencing nucleic acid and a method of sequencing nucleic acid using the same.

2. Description of the Related Art

Nucleic acid sequencing refers to sequencing methods for determining the order of the nucleotide bases—adenine, guanine, cytosine, and thymine—in a molecule of deoxyribonucleic acid (DNA). Conventional methods of sequencing nucleic acid are classified into a chain termination method, originally developed by Frederick Sanger, and a chemical degradation method developed by Maxam and Gilbert. According to these methods, DNA fragments are separated by size using high-resolution gel electrophoresis resolving each single nucleotide. Since these processes are limited by the size of the DNA, sequencing a target nucleic acid is an expensive and time-consuming process, and many target sequences cannot be analyzed at the same time.

According to another known method of sequencing nucleic acid, nucleic acid may be sequenced by ligating a probe with a portion detectable by a nuclease with a target nucleic acid, detecting a fluorescent label, cleaving the probe using the nuclease, and repeating these processes. According to another known method of sequencing nucleic acid, nucleic acid may be sequenced by ligating an oligonucleotide having different 3' bases and four 5' ends with a fluorescent label and a phosphorothiolate bond with a target nucleic acid, measuring a fluorescence, cleaving the oligonucleotide, and repeating these processes. However, these known methods are complicated, and thus specificity and accuracy of sequencing nucleic acid may not be high.

Thus, there is still a need to develop a method of efficiently analyzing the sequence of a target nucleic acid.

SUMMARY

Disclosed herein is a magnetic particle on which a plurality of single-stranded nucleic acids are immobilized.

In one embodiment, a magnetic particle on which a plurality of single-stranded nucleic acids are immobilized, wherein the plurality of single-stranded nucleic acids are immobilized on the magnetic particle through ends of the nucleic acid, and each of the plurality of single-stranded nucleic acids comprises a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

In one embodiment, a magnetic particle on which a plurality of single-stranded nucleic acids are immobilized, wherein the plurality of single-stranded nucleic acids are immobilized on the magnetic particle through ends of the nucleic acid, and each of the plurality of single-stranded nucleic acids comprises a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

In another embodiment, a group of magnetic particles on which a plurality of single-stranded nucleic acids are immobilized, wherein the plurality of single-stranded nucleic acids are immobilized on the magnetic particles through ends of the nucleic acid, and each of the plurality of single-stranded nucleic acids comprises a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region, wherein at least two of the magnetic particles have first regions with different sequences and detectable labels distinguished from each other according to the sequence of the first region.

In still another embodiment, a method of sequencing a target nucleic acid, the method comprising mixing a target nucleic acid having a sequence to be detected, a complementary nucleic acid having a sequence partially complementary to the sequence of the target nucleic acid, and a magnetic particle on which a plurality of single-stranded nucleic acids are immobilized; and hybridizing the target nucleic acid with the complementary nucleic acid, and the target nucleic acid with the single-stranded nucleic acid immobilized on the magnetic particle; adding a ligase to the hybridized mixture to ligate the complementary nucleic acid, which is complementarily hybridized with the single-stranded target nucleic acid, with the single-stranded nucleic acid immobilized on the magnetic particle and hybridized with the single-stranded target nucleic acid adjacent to the complementary nucleic acid; isolating a magnetic particle from the ligated product which is hybridized with the single-stranded target nucleic acid adjacent to the complementary nucleic acid; and identifying a detection signal from the magnetic particle of the isolated product and determining a sequence, which is complementary to the sequence of the first region of the single-stranded nucleic acid immobilized on the magnetic particle and identified from the detection signal, as a portion of the sequence of the target nucleic acid, wherein the plurality of single-stranded nucleic acids are immobilized on the magnetic particle through ends of the nucleic acid, and each of the plurality of single-stranded nucleic acids comprises: a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

In another embodiment, an apparatus for sequencing a target nucleic acid, the apparatus comprising a magnetic particle on which a plurality of single-stranded nucleic acids are immobilized, wherein the plurality of single-stranded nucleic acids are immobilized on the magnetic particle through ends of the nucleic acid, and each of the plurality of single-stranded nucleic acids comprises a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

BRIEF DESCRIPTION OF THE DRAWINGS

These and/or other aspects, advantages and features of the invention will become apparent by describing in further detail exemplary embodiments thereof with reference to the attached drawings, in which.

DETAILED DESCRIPTION

Figure 1:
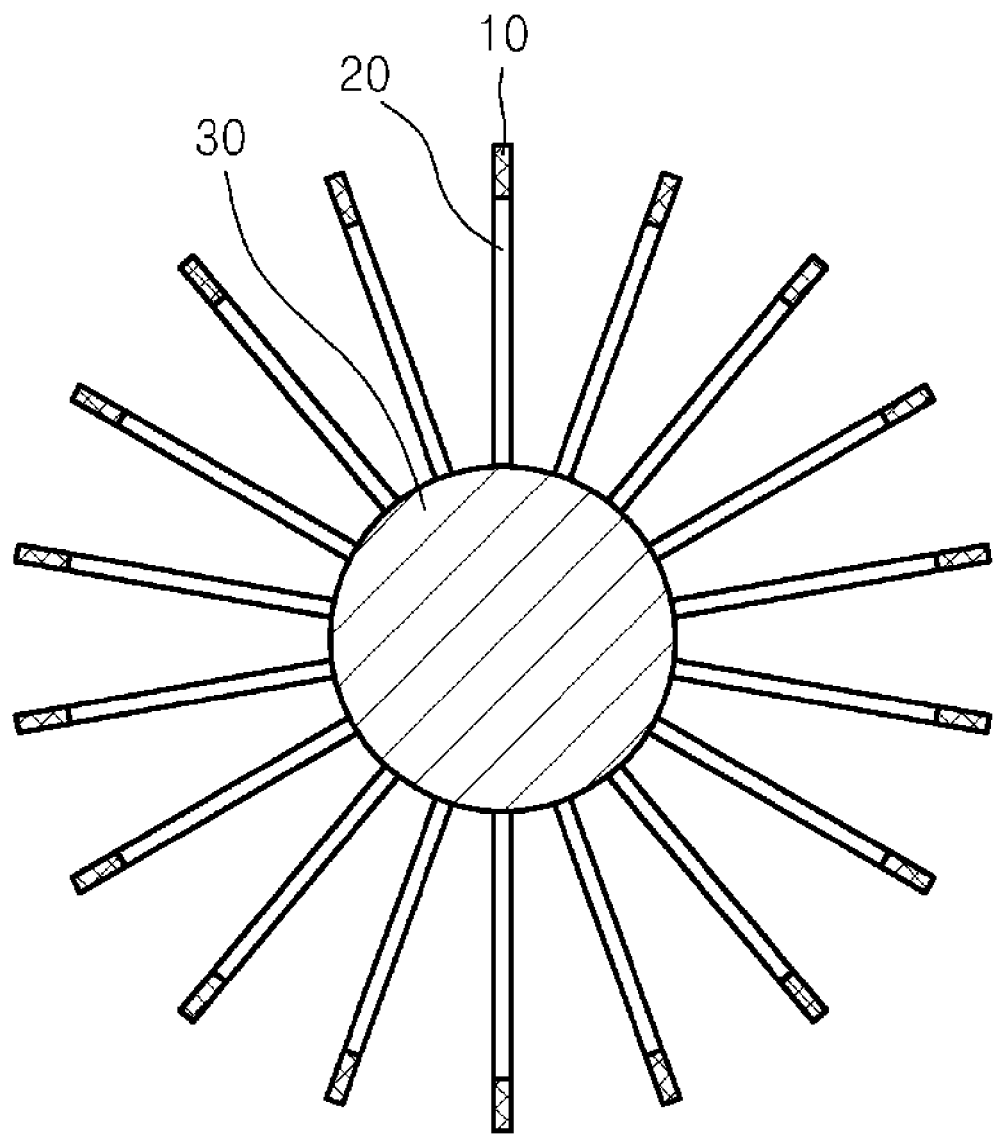
FIG. 1 is a diagram illustrating an exemplary structure of a magnetic particle for sequencing a target nucleic acid.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art.

It will be understood that when an element is referred to as being "on" or "connected to" another element, the element can be directly on or connected to another element or intervening elements. In contrast, when an element is referred to as being "directly on" or "directly connected to" another element, there are no intervening elements present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the disclosure.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Reference will now be made in detail to embodiments, examples of which are illustrated in the accompanying drawings.

Disclosed herein is a magnetic particle on which a plurality of single-stranded nucleic acids are immobilized.

In one embodiment, a group of magnetic particles on which a plurality of single-stranded nucleic acids are immobilized.

In another embodiment, a method of sequencing a target nucleic acid using the magnetic particle on which a plurality of single-stranded nucleic acids are immobilized is provided.

In another embodiment, an apparatus for sequencing a target nucleic acid including a magnetic particle on which a plurality of single-stranded nucleic acids are immobilized is provided.

One embodiment provides a magnetic particle on which a plurality of single-stranded nucleic acids are immobilized, wherein the plurality of single-stranded nucleic acids are immobilized on the magnetic particle through ends of the nucleic acids, and each of the plurality of single-stranded nucleic acids includes: a first region having the same nucleotide sequence on the distal end of the nucleic acid from the magnetic particle; and a second region having a random nucleotide sequence from a nucleotide on the proximal end of the nucleic acid from the magnetic particle to a nucleotide adjacent to the proximal end of the first region.

As used herein, the term "magnetic particle" refers to a particle having magnetic properties and that moves in a magnetic field. The magnetic properties may be paramagnetic properties. The magnetic particle may be a metal material, a magnetic material, or a magnetic alloy. The metal material may include at least one selected from the group consisting of Pt, Pd, Ag, Cu, and Au. The magnetic material may include at least one selected from the group consisting of Co, Mn, Fe, Ni, Gd, Mo, $MM'_2O_4$, and $M_xM_y$, wherein M and M' are each independently Co, Fe, Ni, Mn, Zn, Gd, or Cr, and $0<x\leq3$ and $0<y\leq5$. The magnetic alloy may include at least one selected from the group consisting of CoCu, CoPt, FePt, CoSm, NiFe, and NiFeCo.

As used herein, the term "nucleic acid" refers to a polymer made up of a plurality of nucleotides. The nucleic acid may include DNA (gDNA and cDNA) and/or RNA, peptide nucleic acid (PNA), or locked nucleic acid (LNA) molecules. The nucleotides, which are the basic building blocks of a nucleic acid molecule, may be natural nucleotides, or nucleotide analogs in which sugar or base is modified. Natural nucleotides include 4 types of nucleotides (A, T, G and C). The abbreviations C, A and G are used to describe both the ribonucleotides and the deoxyribonucleotides, according to context. The abbreviation T is used to describe the deoxyribonucleotide.

Nucleic acid immobilized on the magnetic particles may be synthesized using methods commonly used in the art. For example, nucleic acids may be prepared by automated solid-phase process using a phosphoramidite method. The synthesis of nucleic acid may be performed using a commercially available nucleic acid synthesizer. Suitable nucleic acids may also be commercially available.

In the synthesis of the first region and the second region of the nucleic acid, the second region may be synthesized using a combination of nucleotides with the same concentration, for example a combination of dATP, dTTP, dGTP, and dCTP respectively having the same concentration, and the first region may be synthesized using one of the nucleotides.

The magnetic particle on which a plurality of single-stranded nucleic acids are immobilized may have a nano- to micro-level dimension. The term "nano- to micro-level" indicates that the length of a line passing the center of gravity of the magnetic particle is in the range of 1 nm to 1000 μm. If the particle has a spherical shape, the dimension indicates a diameter of the sphere. The dimension may be in the range of about 1 nm to about 10 μm, or about 1 nm to about 1000 nm.

In one embodiment, the first region includes nucleotides of the distal end of the nucleic acid from the magnetic particle. In one embodiment, the first regions of a plurality of single-stranded nucleic acids immobilized on a single magnetic particle may have the same nucleotide sequence. The first region is complementarily hybridized with the target nucleic acid to determine the sequence of the target nucleic acid. The first region may include 1 to 5 nucleotides.

In one embodiment, at least one phosphodiester bond of the first region may be substituted with a bond which cannot be cleaved by an exonuclease. The bond includes a modified phosphate backbone that is not cleaved by an exonuclease. For example, the bond may be phosphorothioate, boranophosphate, methylphosphonate, phosphorodithioate, phosphoramidothioate, phosphoramidite, phosphordiamidate, alkyl phosphotriester, formacetal, or an analog thereof, but is not limited thereto. Due to the bond of the first region, the first region is not removed by the exonuclease, while the second region is selectively removed by the exonuclease.

The nucleic acid is immobilized on the magnetic particle, and the length of the nucleic acid is not limited. For example, the length of the nucleic acid may be determined in consideration of the size of the magnetic particle and the sequence of the target nucleic acid. For example, the nucleic acid may have 5 to 100 bp.

In one embodiment, the nucleic acid may be immobilized on the magnetic particle through a bond which is cleaved by a method that does not cleave the phosphodiester bond of the nucleic acid. For example, the cleavable bond may be a bond that is cleaved by photodegradation or chemical degradation, and the method may be using light or a chemical substance.

A bond cleavable by photodegradation may be 2-nitrobenzyl, benzylamine, benzylcarbonyl, 3-nitrophenyl, phenacyl, 3,5-dimethoxybenzoinyl, 2,4-dinitrobenzenesulphenyl, or a derivative thereof, but is not limited thereto. In addition, a bond cleavable by the chemical degradation may be allyl, disulfide, or acid labile group, but is not limited thereto. The photodegradation and chemical degradation are disclosed in U.S. Pat. Nos. 4,542,225 and 4,625,014.

The 3' end or 5' end of the nucleic acid may be immobilized on the magnetic particle.

The number of the plurality of nucleic acids may vary according to the size of the magnetic particle. For example, the number of the nucleic acids immobilized on the magnetic particle may be in the range of about 10 to about 10,000.

The plurality of nucleic acids may be immobilized on the magnetic particle through a covalent or non-covalent bond.

In one embodiment, the plurality of nucleic acids may be immobilized on the magnetic particle through a mediating substance, for example, a chemical substance such as a reactive functional group. Any reactive functional group that is commonly used in the art may be used, and examples of the reactive functional group are a haloacetyl group, an amine group, a thiol group, a phosphate group, a carboxyl group, or a combination thereof, but is not limited thereto.

In addition, the nucleic acid may bind to the mediating substance on the magnetic particle through a linker. The term "linker" used herein generally indicates a portion attached to an oligonucleotide by a covalent or non-covalent bond through sugar, base, or backbone. The linker may be attached to the 5' and/or 3' end nucleotide of the oligonucleotide. The linker may be a non-nucleotide linker or nucleotide linker.

The term "non-nucleotide linker" used herein generally indicates a chemical portion other than a nucleotide binding portion which may be attached to the oligonucleotide through a covalent or non-covalent bond. For example, the non-nucleotide linker may have a length ranging from about 2 angstroms (Å) to about 200 Å, and may be a cis or trans type. For example, the non-nucleotide linker may be an organic portion having a functional group used for the attachment to the oligonucleotide. This attachment may be achieved by a stable covalent bond. For example, the non-nucleotide linker may be an alkyl linker or an amino linker. The alkyl linker may be a branched or non-branched, cyclic or acylic, substituted or unsubstituted, saturated or unsaturated, chiral, achiral or racemic mixture. For example, the alkyl linker may have 2 to 18 carbon atoms. The alkyl linker may include at least one functional group selected from the group consisting of, but not limited to, a hydroxyl group, an amino group, a thiol group, a thioether group, an ether group, an amide group, a thioamide group, an ester group, an urea group, and a thioether group. The alkyl linker may include 1-propanol linker, 1,2-propanediol linker, 1,2,3-propantriol linker, 1,3-propandiol linker, triethylene glycol hexaethylene glycol linker (e.g., [—O—CH$_2$—CH$_2$—]$_n$, (n=1-9)), methoyl linker, ethyl linker, propyl linker, butyl linker, or hexyl linker.

The covalent bond may be formed by various bonds such as a disulfide bond, imine bond, ester bond, or amide bond. The non-covalent bond may include an ionic bond, hydrogen bond, electrostatic interaction, π-stacking, hydrophobic/hydrophilic interaction, or the like.

In one embodiment, the magnetic particle on which the plurality of single-stranded nucleic acids are immobilized may include a detectable label.

The term "detectable label" used herein refers to an atom or a molecule used to specifically detect a molecule or substance including the label among the same type of molecules or substances without the label. The detectable label may be, for example, a colored bead, an antigen determinant, enzyme, hybridizable nucleic acid, chromophore, fluorescent material, phosphorescent material, electrically detectable molecule, molecule providing modified fluorescence-polarization or modified light-diffusion, quantum dot, or the like. In addition, the detectable label may be radioactive isotopes such as $P^{32}$ and $S^{35}$, a chemiluminescent compound, labeled binding protein, heavy metal atom, a spectroscopic marker such as a dye, or a magnetic label. The dye may be quinoline dye, triarylmethane dye, phthalene, azo dye, or cyanine dye, but is not limited thereto. The fluorescent material may be fluorescein, phycoerythrin, rhodamine, lissamine, or Cy3 or Cy5 (Pharmacia), but is not limited thereto. Meanwhile, the detectable label may be contained in the magnetic particle on which the plurality of single-stranded nucleic acids are immobilized, or in the plurality of single-stranded nucleic acids, and thus the magnetic particle on which the single-stranded nucleic acids are immobilized may be detected.

In another embodiment, a group of magnetic particles, wherein at least two of the magnetic particles have first regions with different sequences and detectable labels distinguished from each other according to the sequence of the first region. Thus, the detectable labels for one group of magnetic particles having first regions with the same sequences may be distinguished from a magnetic particles having first regions with the different sequences compared with the sequences on other groups of magnetic particles.

The magnetic particles contained in the group are described above. The group may include 4 types of magnetic particles including a first region having a single nucleotide, each of which include one of the 4 types of nucleotides (A, T, G and C). In this regard, the 4 types of magnetic particles may include detectable labels distinguished from each other.

In addition, the group may include magnetic particles including a first region having two nucleotides with 16 nucleotide sequences that are combinations of 2 nucleotides. Thus, in one embodiment, a group of magnetic particles includes 16 types of magnetic particles, wherein each of the 16 types of magnetic particles comprise a first region having a combination of two nucleotides. Each of the 16 types of magnetic particles has a different combination of two nucleotides. In this regard, the 16 types of magnetic particles may include detectable labels distinguished from each other.

Additionally, the group may include magnetic particles including a first region having "n" nucleotides. If the number of nucleotides of the first region is n, the group may include magnetic particles with $4^n$ nucleotide sequences.

Another embodiment provides a method of sequencing a target nucleic acid, the method including: mixing a target nucleic acid having a sequence to be determined, a complementary nucleic acid having a sequence partially complementary to the sequence of the target nucleic acid, and a magnetic particle on which a plurality of single-stranded nucleic acids are immobilized; hybridizing the target nucleic acid with the complementary nucleic acid, and the target nucleic acid with the single-stranded nucleic acids immobilized on the magnetic particle; adding a ligase to the hybridized mixture to ligate the complementary nucleic acid, which is complementarily hybridized with the single-stranded target nucleic acid, with the single-stranded nucleic acid immobilized on the magnetic particle, which is hybridized with the single-stranded target nucleic acid adjacent to the complementary nucleic acid; isolating a magnetic particle from the ligated product which is hybridized with the single-stranded target nucleic acid adjacent to the complementary nucleic acid; and identifying a detection signal from the isolated magnetic particle and determining a sequence, which is complementary to the sequence of the first region of the single-stranded nucleic acid immobilized on the magnetic particle and identified from the detection signal, as a portion of the sequence of the target nucleic acid, wherein the plurality of single-stranded nucleic acids are immobilized on the magnetic particle through ends of the nucleic acid, and each of the plurality of single-stranded nucleic acids includes: a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

The method may further include modifying at least one selected from the group consisting of 3' end and 5' end of the target nucleic acid such that an exonuclease does not have 3'→5' or 5'→3' activity, before the hybridization. For example, the target nucleic acid may be modified by adding a protection group to the 3' end or 5' end of the target nucleic acid in order to inhibit the function of the exonuclease. In addition, the modification may include immobilizing at least one selected from the group consisting of the 3' end or 5' end of the target nucleic acid on a solid support.

The method of sequencing the target nucleic acid will be described in more detail below, by referring to the figures.

First, the method includes mixing a target nucleic acid having a sequence to be detected, a complementary nucleic acid having a sequence partially complementary to the sequence of the target nucleic acid, and a magnetic particle on which a plurality of single-stranded nucleic acids are immobilized, and hybridizing the target nucleic acid with the complementary nucleic acid, and the target nucleic acid with the single-stranded nucleic acids immobilized on the magnetic particle.

The term "complementary" used herein indicates that a nucleic acid has complementary properties sufficient for the nucleic acid to be hybridized with a target nucleic acid under a specific hybridization or annealing condition. The term "complementary" means "partial" complimentarity, in which only some of the nucleic acids' bases are matched according to the base pairing rules. Alternatively, "complementary" may be "complete" or "total" complementarity between the nucleic acids. Thus, the term "complementary" is different from the "perfectly complementary". The complementary nucleic acid may be complementarily hybridized with a portion of the target nucleic acid and/or the nucleotides of the second region immobilized on the magnetic particle may be selectively hybridized with the target nucleic acid. In this regard, the hybridized sequence may have one or more mismatch base sequences. The complementary nucleic acid may be a sequence completely complementary to a continuous nucleotide segment of the target nucleic acid having a length corresponding to that of the complementary nucleic acid.

Conditions for the hybridization may be determined according to Joseph Sambrook, et al., *Molecular Cloning, A Laboratory Manual*, Cold Spring Harbor Laboratory Press, Cold Spring Harbor, N.Y. (2001). A stringent condition for the hybridization may be determined by controlling temperature, ionic strength (concentration of a buffer solution), and the existence of a compound such as an organic solvent. Such a stringent condition may vary according to the hybridized sequence.

The target nucleic acid may be genome DNA, mRNA, cDNA, or amplified DNA by the amplification, but is not limited thereto. In one embodiment, the target nucleic acid may be immobilized on a solid support. The "solid support" indicates a solvent-insoluble substrate that may form a bond, e.g., a covalent bond, with a variety of compounds. The solid support may include glass, quartz, silicon, an acrylamide derivative, agarose, cellulose or nylon in the shape of beads, a flat panel, or well, but is not limited thereto.

The solid support may include a plurality of target nucleic acid samples. For example, if the solid support is a flat panel such as a microarray, a plurality of target nucleic acids with different base sequences may be immobilized on the flat panel to analyze the sequence of a large amount of target nucleic acids at a time. In addition, a single type of target nucleic acid may be immobilized on a single solid support. In addition, at least one molecule of a single target nucleic acid may be immobilized on a single solid support. For example, since a plurality of single-stranded nucleic acids are immobilized on the magnetic particle, the detectable label contained in the magnetic particle may generate an intense signal. Thus, if a small number of target nucleic acids, e.g., if a single target nucleic acid molecule is immobilized on the solid support, the sequence may be determined with high yield.

The complementary nucleic acid may be located within a specific length from the 3' end or 5' end of the target nucleic acid. For example, the complementary nucleic acid may be located within about 5 to about 200 nucleotides, about 20 to about 150 nucleotides, or about 50 to about 100 nucleotides, from the 3' end or 5' end of the target nucleic acid.

The complementary nucleic acid is directly ligated with nucleotides of a first region of the plurality of nucleic acids immobilized on the magnetic particle. If the distal end of the first region from the magnetic particle is the 5' or 3' end, the 3' or 5' end of the complementary nucleic acid hybridized with a portion of the target nucleic acid is respectively ligated with the 5' or 3' end of the first region. In this regard, the 5' or 3' end of the complementary nucleic acid may include a protection group for inhibiting the function of the exonuclease. For example, at least one phosphodiester bond of the complementary nucleic acid may be substituted with a bond such as a thiodiester bond that is not cleaved by the exonuclease.

The length of the complementary nucleic acid may vary according to the length of the target nucleic acid. The length of the complementary nucleic acid is less than that of the target nucleic acid in order to sequence the target nucleic acid. The complementary nucleic acid may include 5 to 100 nucleotides.

The hybridization may be performed by simultaneously or sequentially mixing the target nucleic acid, the complementary nucleic acid, and the magnetic particle to simultaneously or sequentially hybridize the target nucleic acid with the complementary nucleic acid, and the target nucleic acid with the single-stranded nucleic acid immobilized on the magnetic particle.

The method also includes adding a ligase to the hybridized mixture to ligate the complementary nucleic acid, which is complementarily hybridized with the single-stranded target nucleic acid, with the single-stranded nucleic acid immobilized on the magnetic particle, and hybridized with the single-stranded target nucleic acid adjacent to the complementary nucleic acid.

It is contemplated that the complementary nucleic acid and the single-stranded nucleic acid immobilized on the magnetic particle are hybridized with the same single-stranded target nucleic acid such that the complementary nucleic acid and the single-stranded nucleic acid immobilized on the magnetic particle are positioned adjacent to each other on the same single-stranded target nucleic acid. The term "hybridized adjacent to" used herein indicates that the complementary nucleic acid and the single-stranded nucleic acid immobilized on the magnetic particle are hybridized with the same single-stranded target nucleic acid, and one end of the complementary nucleic acid is ligated with one end of the single-stranded nucleic acid immobilized on the magnetic particle which faces the complementary nucleic acid using a ligase by a phosphate group contained in the complementary nucleic acid or the single-stranded nucleic acid immobilized on the magnetic particle or by a phosphate group introduced into the complementary nucleic acid or the single-stranded nucleic acid immobilized on the magnetic particle. A single-stranded nucleic acid immobilized on the magnetic particle which has a first region with a sequence completely complementary to the sequence of the target nucleic acid at a region flanking the sequence of the target nucleic acid hybridized with the complementary nucleic acid. The first region participates in the hybridization between the single-stranded target nucleic acid and the single-stranded nucleic acid immobilized on the magnetic particle. In the magnetic particle, a nucleic acid having a second region with a sequence completely complementary to the sequence of the flanking region participates in the hybridization. That is, since the second region has a random sequence, the magnetic particle having a large number of the nucleic acids having a second region with a sequence completely complementary to the sequence of the flanking region participates in the hybridization. In view of probability, if 100 nucleic acid molecules are immobilized on a single magnetic particle, the second region of the nucleic acid immobilized on the magnetic particle may include up to 3 completely complementary sequences, but is not limited thereto.

The term "ligase" used herein is a general term for enzymes that catalyze the joining of two nucleic acid molecules forming a covalent bond. That is, the ligase catalyzes a phosphodiester bond between a phosphate group at the 5' end of a nucleotide and a hydroxyl group at the 3' end of another adjacent nucleotide to ligate the nucleotides. Thus, only when the complementary nucleic acid hybridized with the target nucleic acid is located adjacent to the first region of the single-stranded nucleic acid immobilized on the magnetic particle, the complementary nucleic acid and the first region of the single-stranded nucleic acid immobilized on the magnetic particle may be ligated by the ligase.

The method further includes isolating a magnetic particle from the ligated product which is hybridized with the single-stranded target nucleic acid adjacent to the complementary nucleic acid.

The isolation may be performed by isolating the magnetic particle from the ligated product by cleaning, centrifugation, filtration, or magnetic force. For example, isolating the magnetic particle may be performed using magnetic force.

In the hybridization product in which the single-stranded target nucleic acid is hybridized with the complementary nucleic acid and the single-stranded nucleic acid immobilized on the magnetic particle which are adjacent to each other, the single-stranded nucleic acid immobilized on the magnetic particle is hybridized with the single-stranded target nucleic acid through the completely complementary sequence of the first region and a selectively complementary sequence of the second region of the single-stranded nucleic acid immobilized on the magnetic particle. Meanwhile, the isolated magnetic particle from the ligated product which hybridized with the single-stranded target nucleic acid adjacent to the complementary nucleic acid is completely separated from or weakly hybridized with the target nucleic acid, and thus the residue (i.e., the magnetic particle) has a binding force different from nucleic acid hybridized with the target nucleic acid. Since the difference between forces applied to the hybridized magnetic particle and the magnetic particle which is not hybridized varies according to the binding forces by controlling the intensity of the magnetic force, the ligated product may be isolated from the magnetic particle from the ligated product which hybridized with the single-stranded target nucleic acid adjacent to the complementary nucleic acid.

The method further includes identifying a detection signal from the magnetic particle of the isolated product and determining a sequence, which is complementary to the sequence of the first region of the single-stranded nucleic acid immobilized on the magnetic particle and identified from the detection signal, as a portion of the sequence of the target nucleic acid.

In the determining the sequence, the identifying the detection signal may be performed by measuring one selected from the group consisting of a magnetic signal, an electric signal, a light emitting signal such a fluorescent or Raman signal, a diffusion signal, and a radioactive signal. The detection signal has been described with reference to the detectable label above.

In one embodiment, the magnetic particle may be a group of a plurality of magnetic particles, wherein at least two of the magnetic particles have first regions with different sequences and detectable labels distinguished from each other according to the sequence of the first region. Thus, the detectable labels for the magnetic particles will be the same for magnetic particles have first regions with the same nucleotide sequences, and the detectable labels for the magnetic particles will differ between magnetic particles have first regions with the different nucleotide sequences, allowing for magnetic particles having different first regions to be distinguished from each other.

For example, the group may include magnetic particles, each including single-stranded nucleic acids with first regions having one of the 4 types of nucleotides (i.e., A, T, G and C) labeled with detectable labels distinguished from each other.

The method may further include cleaving the bond between the nucleic acid immobilized on the magnetic particle and ligated with the complementary nucleic acid and the magnetic particle to expose the end of the nucleic acid so as to be cleaved by an exonuclease after determining the sequence. The cleavage may be performed by irradiating light or applying a chemical substance to the bond. The light may be X-rays or UV rays. The cleavable bond has been described above.

According an embodiment, the second region of the single-stranded nucleic acid immobilized on the magnetic particle may be removed by the exonuclease, wherein a phosphodiester bond in the first region of the nucleic acid is modified so as not to be cleaved by an exonuclease.

The first region of the single-stranded nucleic acid of the magnetic particle may include two or more nucleotides. After a portion of the sequence is determined by detecting the signal, nucleotides of the second region are removed in order to further determine a base sequence adjacent to the determined sequence. The nucleotides of the second region may be removed by the exonuclease. The nucleotide of the first region may not be removed by the exonuclease. Thus, at least one nucleotide of the first region is modified to include a bond that is not cleaved by the exonuclease. The bond that is not cleaved by the exonuclease has been described above.

The method may include the hybridizing, ligating, isolating, determining, cleaving, and removing operations which are repeated.

The base sequence of the oligonucleotide including a plurality of bases contained in the target nucleic acid may be determined by repeating the process described above.

In another embodiment, an apparatus for sequencing a target nucleic acid, the apparatus including: a magnetic particle on which a plurality of single-stranded nucleic acids are immobilized, wherein the plurality of single-stranded nucleic acids are immobilized on the magnetic particle through ends of the nucleic acid, and each of the plurality of single-stranded nucleic acids includes: a first region having the same nucleotide sequence from the distal end of the nucleic acid from the magnetic particle; and a second region having a random nucleotide sequence from a nucleotide of the proximal end of the nucleic acid from the magnetic particle to a nucleotide adjacent to the proximal end of the first region.

The apparatus may further include at least one reagent used to sequence the nucleic acid, for example, a buffer solution, an exonuclease, a ligase, ATP, or a chemical substance capable of cleaving the bond between the magnetic particle and the nucleic acid. The apparatus may be prepared in a plurality of packages or compartments including the components or the apparatus may be fixed on a substrate.

In the apparatus, the magnetic particle may be a group of a plurality of magnetic particles, wherein at least two of the magnetic particles have first regions with different sequences and detectable labels distinguished from each other according to the sequence of the first region.

Since the apparatus includes the magnetic particle on which the plurality of single-stranded nucleic acids are immobilized that has been described above a description of the magnetic particle will be omitted herein.

Hereinafter, one or more embodiments of the present invention will be described in detail. However, these embodiments are not intended to limit the purpose and scope of the present invention.

FIG. 1 is a diagram illustrating an exemplary structure of a magnetic particle 30 on which nucleic acids are immobilized for sequencing a target nucleic acid. In one embodiment, the nucleic acids immobilized on the magnetic particle are single-stranded nucleic acids. The magnetic particle 30 on which nucleic acids are immobilized may have a diameter of 100 nm or less. The magnetic particle 30 has paramagnetic properties and is connected to nucleic acids including a first region 10 and a second region 20. In one embodiment, the nucleic acid may be DNA. The DNA may be immobilized on the surface of the magnetic particle 30 via a chemical bond by a linker. A plurality of DNA molecules may be immobilized on the surface of a single magnetic particle. 1 or 2 bases at the ends of the first region 10 consisting of nucleotides A, C, G, or T, or a combination thereof, are used to recognize the sequence of a target nucleic acid.

Figure 2:
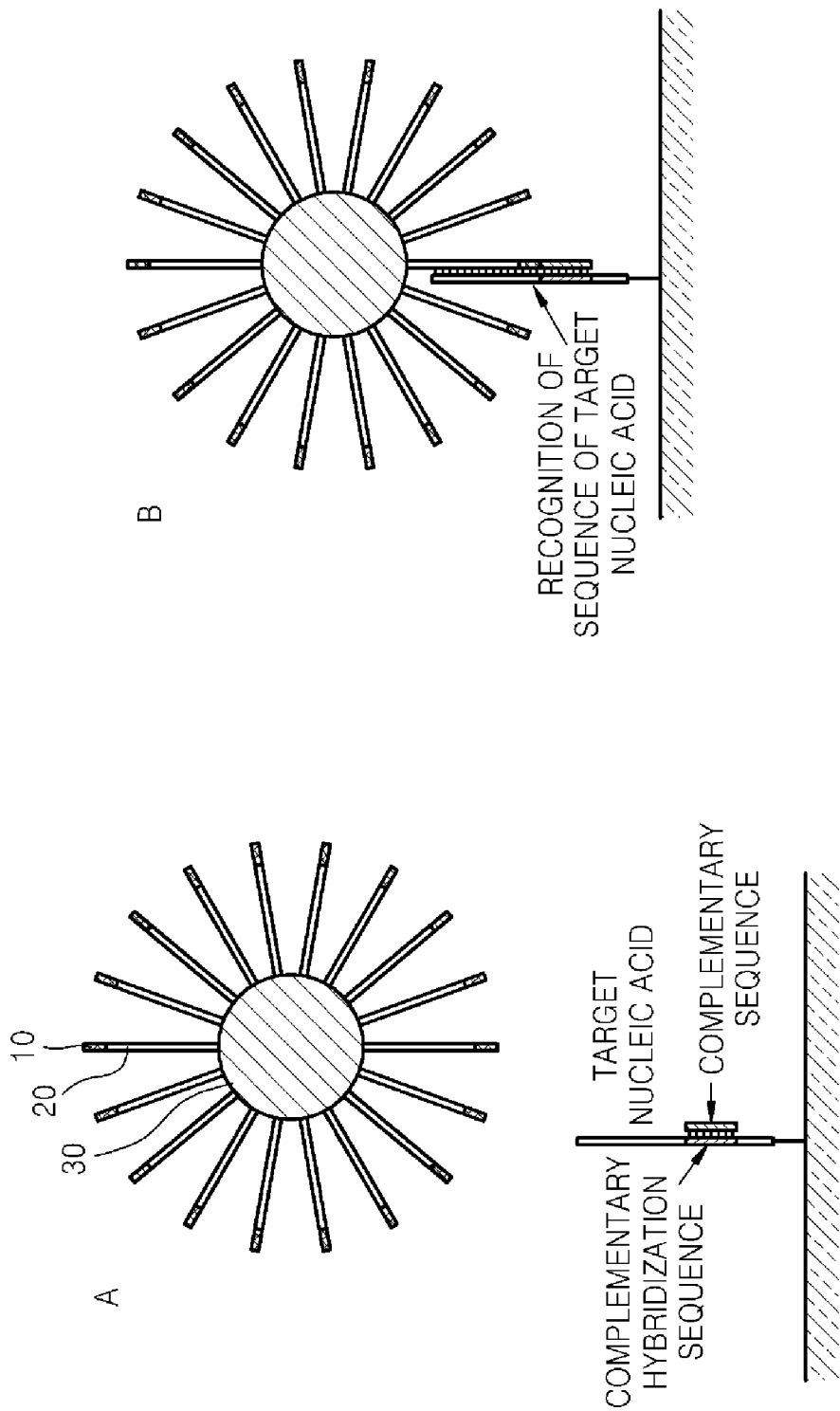
FIG. 2 is a diagram illustrating recognition of a base sequence of a target nucleic acid using the magnetic particle.

FIG. 2 is a diagram that illustrates an example of the recognition of a base sequence of a target nucleic acid using the magnetic particle 30. The target nucleic acid may be a single-stranded DNA molecule which has a sequence complementary to the complementary nucleic acid. As shown in panel A, the through the target nucleic acid is hybridized with a complementary nucleic acid. In one embodiment, the target nucleic add immobilized to surface of a substrate, as shown in Panels A and B. Panel B illustrates a DNA immobilized on the magnetic particle 30 is complementarily hybridized with the target nucleic acid and ligated with the complementary nucleic acid. In this regard, the nucleic acid immobilized on the magnetic particle 30 is ligated with the complementary nucleic acid by a ligase only when a sequence of the target nucleic acid adjacent to the sequence complementarily hybridized with the complementary nucleic acid is complementary to that of the nucleic acid immobilized on the magnetic particle. Thus, detecting a signal from the magnetic particle 30 may reveal information on the sequence of the target nucleic acid. For example, a fluorescent molecule may be attached to the surface of the magnetic particle 30 such that the magnetic particle 30 has different fluorescence according to 1 or 2 base sequences adjacent to the complementary nucleic acid. Alternatively, information on the sequence of a target nucleic acid may be obtained by preparing a magnetic particle emitting fluorescence by coating a magnetic material on a fluorescent nano particle, and detecting a fluorescent signal from the magnetic particle.

Figure 3:
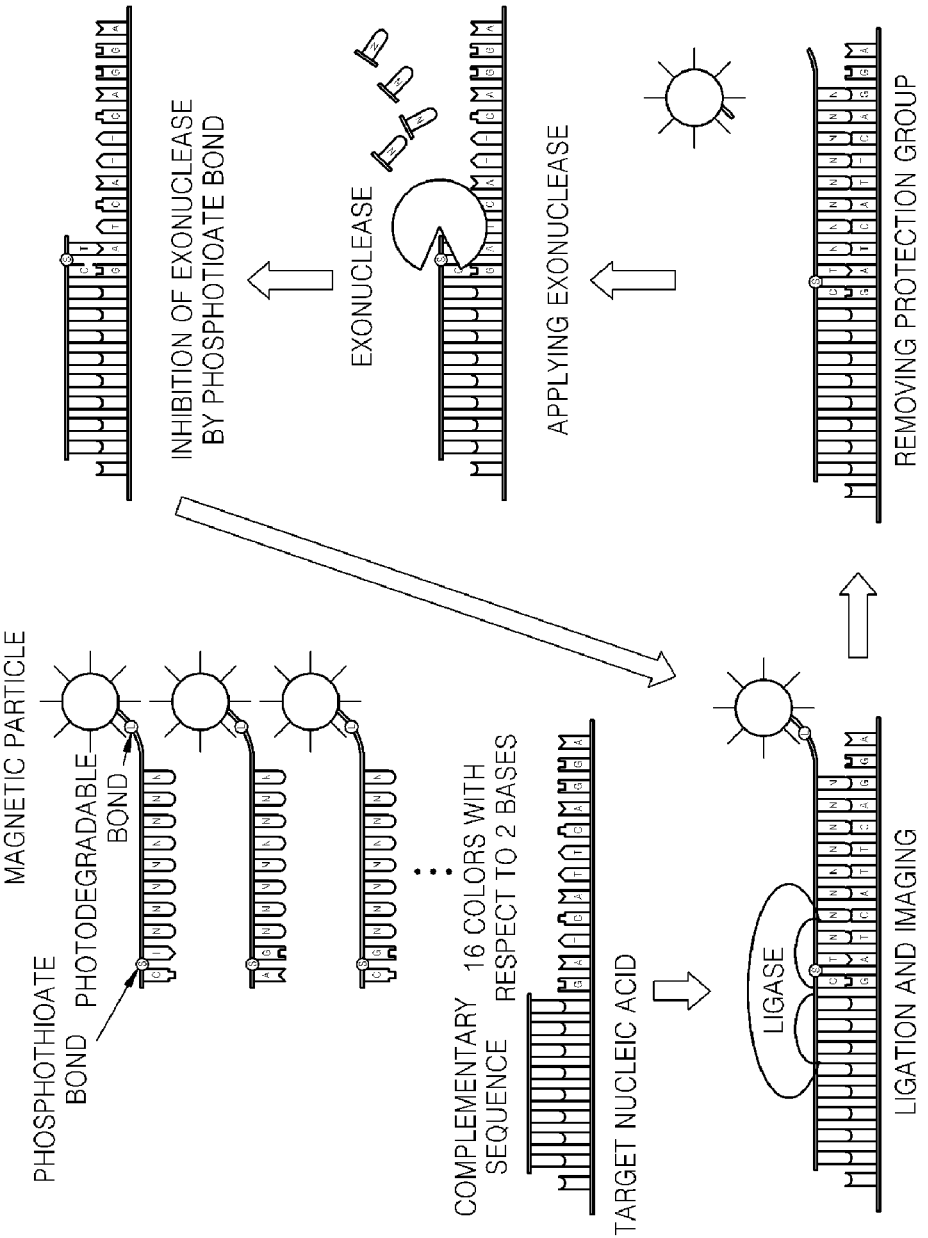
FIG. 3 is a diagram illustrating an exemplary process of analyzing the sequence of a target nucleic acid by the extension of nucleotides.

FIG. 3 is a diagram illustrating an exemplary process of analyzing the sequence of a target nucleic acid by the extension of nucleotides. According to the embodiment illustrated in FIG. 3, the sequence of target nucleic acid may be obtained by sequentially extending nucleotides. For this, the magnetic particle used to identify the base sequence is separated from the nucleic acid, and nucleotides of the complementary nucleic acid are extended. FIG. 3. shows a group of magnetic particle having a plurality of single-stranded nucleic acids immobilized on the magnetic particle. The single-stranded nucleic acids may be DNA. The DNA includes a first region of nucleotides on the distal end of the DNA from the magnetic particle. The first region comprising 1 to 5 nucleotides. The group of magnetic particles may include 4 types of magnetic particles including a first region having a single nucleotide, each of which include one of the 4 types of nucleotides (A, T, G and C) at the terminal end. As shown in FIG. 3, a nucleotide bond at the first region, which is a base sequence recognition region, of DNA immobilized on the magnetic particle may be a bond that is not cleaved by an exonuclease, such as, for example, a phosphorothioate bond. Additionally, FIG. 3 shows that the DNA includes a second region of nucleotides on the proximal end of the DNA from the magnetic particle. The length of the nucleic acid may be determined in consideration of the size of the magnetic particle and the sequence of the target nucleic acid. For example, the nucleic acid may have 5 to 100 bp. The second region of nucleotides is immobilized to the magnetic particles using a linker through a bond which is cleaved by a method that does not cleave the phosphodiester bond of the nucleic acid. For example, the cleavable bond may be a bond that is cleaved by photodegradation or chemical degradation. For the embodiment shown in FIG. 3, a functional group that is cleaved by light generated using a chemical substrate is applied to the bond between the second region and a linker.

According to FIG. 3, the magnetic particle on which a plurality of single-stranded nucleic acids are immobilized is mixed with a target nucleic acid having a sequence to be detected and a complementary nucleic acid having a sequence partially complementary to the sequence of the target nucleic acid. After mixing, the target nucleic acid is hybridized with the complementary nucleic acid, and the target nucleic acid is hybridized with the single-stranded nucleic acids immobilized on the magnetic particle. Then, a ligase is added to the hybridized mixture to ligate the complementary nucleic acid with the single-stranded nucleic acid immobilized on the magnetic particle, and hybridized with the single-stranded target nucleic acid adjacent to the complementary nucleic acid. After completing the ligation reaction, the magnetic particle is isolated from the ligated product by cleaving the bond between the magnetic particle and DNA. If the bond between the magnetic particle and DNA is formed by a bond cleavable by photodegradation, then light generated by a chemical substance may be used to cleave the bond. Next, an exonuclease which degrades DNA is added to the mixture. In this regard, the exonuclease will degrade the nucleotides of the second region but may not degrade the nucleic acids in the first region because of the phosphothioate bond. The complementary nucleic acid ligated to the first region remains hybridized to the target nucleic acid. Following degradation of the DNA with the exonuclease, the process is repeated.

After two nucleotides are extended as described above, DNA immobilized on another magnetic particle is ligated with the nucleotide of the extended complementary nucleic acid. Then, the sequence of the target nucleic acid is recognized. By repeating the cycle, nucleotides are extended to recognize the sequence of the target nucleic acid. The magnetic particles have 16 different fluorescence wavelengths in order to identify the base sequence of the two nucleotides. The information on the base sequence may be obtained using, for example, a method of recognizing difference of peak wavelength using fluorescence nano particles having a narrow wavelength range or a method of classifying distribution of fluorescent wavelength by attaching a variety of organic fluorescent materials having various wavelengths to magnetic particles in different ratios. In addition, in order to sequence a single base at a time, the base is sequenced using 4 fluorescent wavelengths, the complementary nucleic acids are detached, a second complementary nucleic acid is hybridized to be spaced by one base, and the signal is detected. Then, the cycle is repeated, and the remaining sequence is analyzed to obtain information on the complete sequence.

According to a general method of sequencing DNA by repeating cycles, nucleic acid binding to organic fluorescent molecules is removed by cleaning since organic fluorescent molecules are used, and fluorescent signals immobilized on the surface of a substrate are detected to analyze the sequence. However, when the magnetic particle is used, nano particles emitting fluorescence from surfaces thereof may be isolated using a magnetic field in the same reaction solution without replacing a reaction solution. For example, fluorescence binding to a target nucleic acid sample adjacent to the surface of the substrate may be selectively detected using total internal reflection fluorescence (TIRF).

Figure 4:
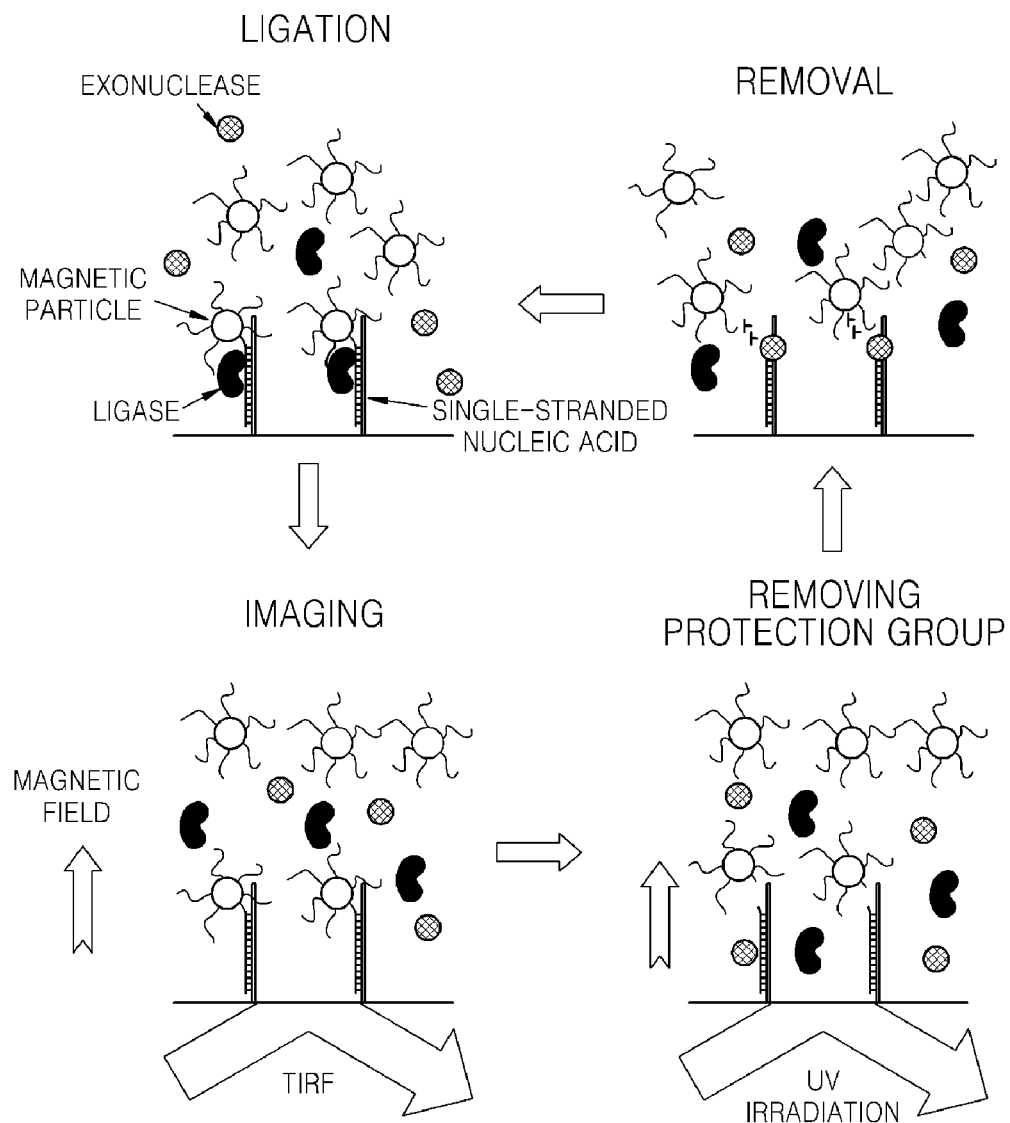
FIG. 4 is a diagram illustrating an exemplary process of analyzing a base sequence of a target nucleic acid at different cycles of a reaction without replacing a reaction solution.

FIG. 4 is a diagram illustrating an exemplary method for analysis of a base sequence of a target nucleic acid at different cycles of a reaction without replacing a reaction solution. For this embodiment, a single-stranded target nucleic acid is immobilized to the surface of a substrate. As described above, during for ligation, the target nucleic having a sequence to be detected is mixed with a complementary nucleic acid and magnetic particles having different fluorescent wavelengths. The magnetic particles have different fluorescent wavelengths according to the nucleotide sequence of the first region. For example, the magnetic particles comprising a first region having the same nucleotide sequence will have detectable labels having identical fluorescent wavelengths. After mixing, the target nucleic acid is hybridized with the complementary nucleic acid, and the target nucleic acid is hybridized with the single-stranded nucleic acids immobilized on the magnetic particle. Then, a ligase is added to the hybridized mixture to ligate the complementary nucleic acid with the single-stranded nucleic acid immobilized on the magnetic particle, and hybridized with the single-stranded target nucleic acid adjacent to the complementary nucleic acid. Following the ligation procedure, unhybridized magnetic particles are removed from the surface of the substrate by a magnetic field. Then, fluorescence of the magnetic particles hybridized with the target nucleic acid which is located close to the surface of the substrate is detected using TIRF. After detecting the magnetic particles hybridized with the target nucleic acid using TIRF, the magnetic particles are detached from DNA by light irradiation. Then, DNA is degraded by an exonuclease in the reaction solution, and the degradation by the exonuclease is stopped at the bond incorporated into the first region that is uncleavable by the exonuclease, for example, a phosphothioate bond. Then, when the application of the magnetic field is terminated, nano particles of the reaction solution move to the surface of the substrate. Thus, a next cycle is started according to the next sequence of the target nucleic acid. The sequence of the target nucleic acid may be determined by repeating these operations, and analyzing images obtained by detected signals.

As described above, according to the one or more of the above embodiments of the present invention, a nucleotide sequence of a target nucleic acid may be efficiently determined using a magnetic particle and a method of sequencing the magnetic particle.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A magnetic particle on which a plurality of single-stranded nucleic acids are immobilized, wherein each of the plurality of single-stranded nucleic acids are immobilized on the magnetic particle through an end of the nucleic acid with a bond that is cleaved by photodegradation or chemical degradation, and each of the plurality of single-stranded nucleic acids comprises: (a) a first region at an end of the nucleic acid distal to the magnetic particle, wherein the first region of each of the plurality of single stranded nucleic acids has the same nucleotide sequence; and (b) a second region adjacent to the first region and proximal to the magnetic particle, wherein the nucleotide sequence of the second region of each of the plurality of single stranded nucleic acids is a random sequence; wherein the first region consists of 1 to 5 nucleotides having at least one bond which is not cleaved by an exonuclease that can remove the second region.

2. The magnetic particle of claim 1, wherein the first region consists of 2 nucleotides.

3. The magnetic particle of claim 1, wherein the magnetic particle on which the plurality of single-stranded nucleic acids are immobilized comprises a detectable label.

4. A group of magnetic particles on which a plurality of single-stranded nucleic acids are immobilized, wherein each of the plurality of single-stranded nucleic acids are immobilized on the magnetic particle through an end of the nucleic acid with a bond that is cleaved by photodegradation or chemical degradation, and each of the plurality of single-stranded nucleic acids comprises:
  (a) a first region at an end of the nucleic acid distal to the magnetic particle, wherein the first region of each of the plurality of single stranded nucleic acids on a single magnetic particle has the same nucleotide sequence; and
  (b) a second region adjacent to the first region and proximal to the magnetic particle, wherein the nucleotide sequence of the second region of each of the plurality of single stranded nucleic acids is a random sequence;
  wherein the first region comprises 1 to 5 nucleotides and at least one bond which is not cleaved by an exonuclease that can remove the second region,
  and wherein at least two of the magnetic particles of the group of magnetic particles have first regions with different sequences and detectable labels distinguished from each other according to the sequence of the first region.

5. The group of magnetic particles of claim 4, wherein the first region comprises a single nucleotide having A, T, G, or C.

6. The group of magnetic particles of claim 4, wherein the group comprises 16 types of magnetic particles, wherein each of the 16 types of magnetic particles comprise a first region having a different combination of two 2 nucleotides.

7. An apparatus for sequencing a target nucleic acid, the apparatus comprising a magnetic particle of claim 1.

8. The apparatus of claim 7 comprising a plurality of magnetic particles of claim 1, wherein at least two of the magnetic particles have first regions with different sequences, and the magnetic particles comprise detectable labels distinguished from each other according to the sequence of the first region.

9. The apparatus of claim 7, wherein the nucleic acid has 5 to 100 nucleotides.

10. The apparatus of claim 7, wherein the 3' end of the nucleic acid is immobilized on the magnetic particle.

11. The apparatus of claim 8, wherein the detectable label is contained in the magnetic particle on which the plurality of single-stranded nucleic acids are immobilized or in the plurality of single-stranded nucleic acids.

12. The apparatus of claim 7, further comprising one or more of an exonuclease, a ligase, ATP, a chemical substance capable of cleaving the bond between the magnetic particle and the nucleic acid, or a buffer solution.

13. The apparatus of claim 7, wherein the magnetic particle has a diameter in the range of about 1 nm to about 1000 nm.

14. The apparatus of claim 7, wherein the first region consists of 2 to 5 nucleotides.

15. The magnetic particle of claim 1, wherein the first region consists of 2 to 5 nucleotides.

16. The magnetic particle of claim 1, wherein the first region comprises a phosphorothioate, boranophosphate, methylphosphonate, phosphorodithioate, phosphoramidothioate, phosphoramidite, phosphordiamidate, alkyl phosphotriester, or formacetal bond.

* * * * *